United States Patent [19]

Karcher et al.

[11] Patent Number: 5,696,223

[45] Date of Patent: Dec. 9, 1997

[54] COPOLYMERIZABLE OXIME ETHERS

[75] Inventors: Michael Karcher, Schwetzingen; Marc Heider, Neustadt; Thomas Rühl, Frankenthal; Jochem Henkelmann, Mannheim, all of Germany

[73] Assignee: BASF Aktiengesellschaft, Ludwigshafen, Germany

[21] Appl. No.: 563,535

[22] Filed: Nov. 28, 1995

[30] Foreign Application Priority Data

Nov. 29, 1994 [DE] Germany .................. 44 42 446.9

[51] Int. Cl.⁶ .................................................. C08G 73/00
[52] U.S. Cl. ...................... 528/422; 526/311; 564/256
[58] Field of Search ................... 528/422; 526/311; 564/256

[56] References Cited

U.S. PATENT DOCUMENTS 5,459,216  10/1995  Bott et al. .......................... 526/311

FOREIGN PATENT DOCUMENTS 617 012   9/1994   European Pat. Off. .
42 19 385  12/1993  Germany .

OTHER PUBLICATIONS

Nedolya et al., *J. Org. Chem.*, USSR, vol. 23, 1987, pp. 1285–1288.

*Primary Examiner*—James J. Seidleck
*Assistant Examiner*—Duc Truong
*Attorney, Agent, or Firm*—Keil & Weinkauf

[57] ABSTRACT

Oxime ethers of the general formula I

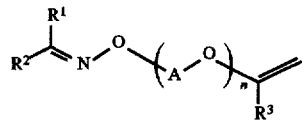

where the variables have the following meanings:

$R^1$, $R^2$ independently of one another hydrogen, $C_1$–$C_{20}$-alkyl, $C_4$–$C_{10}$-cycloalkyl, $C_6$–$C_{10}$-aryl or together a bridge of 3–14 carbon atoms, $R^3$ hydrogen, $C_1$–$C_6$-alkyl or phenyl which is unsubstituted or carries inert substituents, n an integer from 1 to 100, A $C_2$–$C_{10}$-alkylene groups which are unsubstituted or carry inert substituents, a process for the preparation thereof and the use thereof as copolymerizable monomers are described.

8 Claims, No Drawings

COPOLYMERIZABLE OXIME ETHERS

The present invention relates to copolymerizable oxime ethers of the general formula I

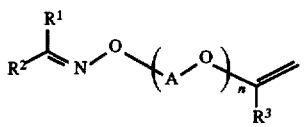

where the variables have the following meanings:

| | |
|---|---|
| $R^1, R^2$ | independently of one another hydrogen, $C_1$–$C_{20}$-alkyl, $C_4$–$C_{10}$-cycloalkyl, $C_6$–$C_{10}$-aryl or together a bridge of 3–14 carbon atoms, |
| $R^3$ | hydrogen, $C_1$–$C_6$-alkyl or phenyl which is unsubstituted or carries inert substituents, |
| n | an integer from 1 to 100, |
| A | $C_2$–$C_{10}$-alkylene groups which are unsubstituted or carry inert substituents. |

The invention furthermore relates to a process for preparing the oxime ethers and to the use thereof in polymeric coating compositions or adhesives.

Polymeric protective coatings or adhesive coatings with good elastic properties, high cohesion and good chemical- and solvent-resistance are prepared in particular through crosslinkable copolymers. For this purpose, a crosslinkable monomer is incorporated in the copolymers by copolymerization.

These monomers ought accordingly to carry a functional group suitable for the copolymerization and one suitable for the crosslinking. DE-A 42 19 385 discloses copolymerizable ethers which carry an acrylate group.

There is a fundamental need for further crosslinking comonomers in order to be able to meet, by variation thereof, the wide variety of demands made on polymeric coating compositions and adhesives. It is furthermore an object of the invention to provide a process which permits such compounds to be prepared in an industrially straight-forward manner and in high yield.

We have found that this object is achieved by the oxime ethers I defined at the outset. We have furthermore found a process for the preparation thereof and the use thereof as copolymerizable monomers.

The oxime ethers carry a crosslinkable oxime group. The radicals $R^1$ and $R^2$ in this group are each, independently of one another, hydrogen or $C_1$–$C_{20}$-alkyl, with $C_1$–$C_6$-alkyl such as methyl, ethyl, n-propyl and n-butyl being preferred. The alkyl groups can be straight-chain or branched. The radicals $R^1$ and $R^2$ are furthermore $C_4$–$C_{10}$-cycloalkyl, of which cyclopentyl and cyclohexyl are preferred. Also suitable are $C_6$–$C_{10}$-aryl groups such as, preferably, phenyl, which may carry inert substituents such as alkyl and alkoxy. The radicals $R^1$ and $R^2$ can together form a bridge with 3–14 carbon atoms, with alkylene bridges being preferred. $R^1$ and $R^2$ particularly preferably are each methyl, are methyl and phenyl or form a $C_5$-alkylene bridge.

The radical $R^3$ on the copolymerizable alkenyl group is preferably hydrogen, but $C_1$–$C_6$-alkyl groups such as methyl and ethyl, and phenyl, are also suitable.

The variable n indicates the number of alkylene oxide units in the oxime ether chain. This number can be from 1 to 100. Short-chain compounds in which n is from 1 to 10 are preferred; n is particularly preferably 1.

The divalent radical A is a straight-chain or branched $C_2$–$C_{10}$-alkylene radical which can carry, for example, aryl groups as inert substituents. A is preferably an ethylene group.

The oxime ethers of the formula I according to the invention are prepared from oxime ether alcohols of the formula II

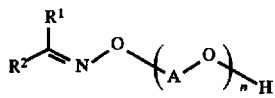

where the variables have the abovementioned meanings. These oxime ether alcohols are known or can be prepared by known methods (e.g. Bachman et al., J. Am. Chem. Soc. 81 (1959) 4223). They are prepared starting from oximes which can be prepared from ketones or aldehydes and hydroxylamine (Houben-Weyl, Methode der Org. Chemie, Thieme Verlag, 1968, Vol. 10/4, pp. 10 et seq.).

The oximes can be reacted with alkylene oxides such as ethylene oxide, propylene oxide and butylene oxide, but also styrene oxide in the presence of a base such as lithium methoxide. In order to obtain n alkylene oxide units in the oxime ether alcohols of the formula II, n equivalents of the appropriate epoxide are reacted with one equivalent of oxime.

The oxime ether alcohols of the formula II are with an alkyne of the formula III

 III $$R^3\text{—}C\equiv CH$$

This alkyne is preferably acetylene, but alkynes such as propyne or phenylacetylene are also suitable. When acetylene is employed, this can be used undiluted or diluted with inert such as nitrogen, methane or argon.

The molar ratio of the oxime ether alcohol II to the alkyne III is generally from 0.05:1 to 1.2:1, preferably 0.2:1 to 0.8:1.

The reaction is carried out in the presence of an inorganic base. Suitable for this purpose are alkali metal and alkaline earth metal hydroxides such as lithium hydroxide, sodium hydroxide and calcium hydroxide, but preferably potassium hydroxide. It is also possible to use alkali metal alcoholates, preferably $C_1$–$C_4$-alcoholates such as sodium methoxide, sodium ethoxide, potassium methoxide and potassium tert-butoxide. As a rule, from 0.005 to 1 mol of base is employed, preferably from 0.02 to 0.3 mol per mole of oxime ether alcohol II.

Although the reaction can be carried out without solvent, it has proven advantageous to use a solvent, with polar aprotic solvents such as dimethyl sulfoxide, phenyl methyl sulfoxide, sulfolane and polyethylene glycols and their ethers being particularly preferred. The amount of the solvent can vary within wide limits and can be from 10 to 90% of the weight of the reaction mixture.

The reaction can be carried out at from 50° to 250° C., preferably from 70° to 120° C., under from 1 to 100 bar.

It is possible to mix the oxime ether alcohols, the base and the solvent and to add the alkyne at the reaction temperature. The reaction is generally complete after 1–36 h. The products can be isolated by distillation in the case of relatively volatile compounds, but longer-chain compounds of the formula I can also be used without further purification. The base which is present in the distillation residue can be returned to the reaction.

The products of the formula I are used as copolymerizable monomers for preparing polymeric coating compositions and adhesives. For this purpose they can be subjected to free-radical or cationic polymerization in a conventional way in amounts of, preferably, from 0.01 to 30% of the total weight of monomers in particular with $C_1$–$C_{10}$-alkyl (meth)acrylates, vinyl esters of carboxylic acids containing from 1 to 20 carbon atoms, an vinyl ethers of $C_1$–$C_{20}$-alcohols such as methyl, ethyl, isobutyl and octadecyl vinyl ethers.

EXAMPLES

Example 1

Preparation of Acetone 2-(Vinyloxy)Ethyloxime

A nitrogen pressure of 5 bar was set up in a 300 ml autoclave containing 75 g (0.64 mol) of acetone 9.4 g (0.17 mol) of KOH and 75 g of sulfolane. At 90° C., acetylene was injected to a total pressure of 20 bar. Consumed acetylene was replaced by subsequent injection. After 24 h, decompression was effected and the reaction discharge was distilled. 88.9 g of acetone 2-(vinyloxy)ethyloxime (97% yield) were with a boiling point of 45° C. (7.5 mbar).

Example 2

Preparation of Acetone 2-(Vinyloxy)Ethyloxime 30 g (0.26 mol) of acetone hydroxyethyloxime, 3.8 g (0.07 mol) of KOH and 120 g of dimethyl sulfoxide were reacted at 90° C. in a similar manner to Example 1. The yield was 84%.

Example 3

Preparation of Acetophenone 2-(Vinyloxy) Propyloxime 30 g (0.16 mol) of acetophenone hydroxypropyloxime, 3.8 g (0.07 mol) of KOH and 120 g of dimethyl sulfoxide were reacted at 90° C. in a similar manner to Example 1. Acetophenone 2-(vinyloxy)propyloxime was isolated in a yield of 78% with a boiling point of 110° C. (5 mbar).

We claim:

1. An oxime ether of the general formula I

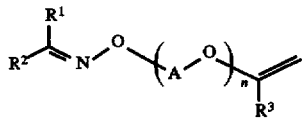

where the variables have the following meanings:

$R^1$, $R^2$ independently of one another hydrogen, $C_1$–$C_{20}$-alkyl, $C_4$–$C_{10}$-cycloalkyl, $C_6$–$C_{10}$-aryl or together bridge of 3–14 carbon atoms, $R^3$ hydrogen, $C_1$–$C_6$-alkyl or phenyl which is unsubstituted or carries inert substituents, n an integer from 1 to 100, A $C_2$–$C_{10}$-alkylene groups which are unsubstituted or carry inert substituents.

2. An oxime ether as claimed in claim 1, where $R^1$ and $R^2$ are each methyl, or are methyl and phenyl, or $R^1$ and $R^2$ form a bridge of 5 carbon atoms.

3. An oxime ether as claimed in claim 1, where $R^3$ is hydrogen.

4. An oxime ether as claimed in claim 1, where n is 1.

5. A process for preparing oxime ethers of the general formula I as claimed in claim 1, which comprises reacting oxime ether alcohols of the general formula II

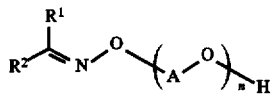

where the variables have the abovementioned meanings, with an alkyne of the general formula III

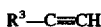

where $R^3$ has the abovementioned meaning, in the presence of an inorganic base.

6. A process as claimed in claim 5, wherein the reaction is carried out in dimethyl sulfoxide or sulfolane.

7. A process as claimed in claim 4, wherein potassium hydroxide or alkali metal alcoholates are used as base.

8. A method for preparing polymeric coating compositions or adhesives which comprises copolymerizing an oxime ether of the formula I as defined in claim 1 with a crosslinking agent.

* * * * *